(12) United States Patent
Grady

(10) Patent No.: US 7,520,277 B1
(45) Date of Patent: Apr. 21, 2009

(54) CPAP ENCLOSURE FOR THE TREATMENT OF SLEEP APNEA

(76) Inventor: Daniel Grady, 575 Yadkin Rd., Southern Pines, NC (US) 28387

( * ) Notice: Subject to any disclaimer, the term of this patent is extended or adjusted under 35 U.S.C. 154(b) by 847 days.

(21) Appl. No.: 10/404,638

(22) Filed: Apr. 1, 2003

(51) Int. Cl.
A62B 17/04 (2006.01)

(52) U.S. Cl. .................................. 128/201.23

(58) Field of Classification Search .............. None
See application file for complete search history.

(56) References Cited

U.S. PATENT DOCUMENTS

| | | | | |
|---|---|---|---|---|
| 2,603,214 A | * | 7/1952 | Taylor | 128/204.15 |
| 3,006,339 A | * | 10/1961 | Smith | 128/204.22 |
| 3,587,574 A | | 6/1971 | Mercer | |
| 4,328,799 A | | 5/1982 | LoPiano | |
| 4,502,481 A | * | 3/1985 | Christian | 128/205.24 |
| 4,727,870 A | | 3/1988 | Krasle | |
| 4,807,616 A | * | 2/1989 | Adahan | 128/204.21 |
| 4,821,709 A | * | 4/1989 | Jensen | 128/204.21 |
| 4,852,598 A | | 8/1989 | Griesenbeck | |
| 4,974,829 A | | 12/1990 | Gamow et al. | |
| 4,989,596 A | * | 2/1991 | Macris et al. | 128/201.28 |
| 5,109,837 A | | 5/1992 | Gamow | |
| 5,193,532 A | | 3/1993 | Moa et al. | |
| 5,199,424 A | * | 4/1993 | Sullivan et al. | 128/204.18 |
| 5,231,979 A | | 8/1993 | Rose et al. | |
| 5,243,971 A | | 9/1993 | Sullivan et al. | |
| 5,245,995 A | | 9/1993 | Sullivan et al. | |
| 5,303,434 A | | 4/1994 | Arnold | |
| 5,353,788 A | | 10/1994 | Miles | |
| 5,398,678 A | | 3/1995 | Gamow | |
| 5,467,764 A | | 11/1995 | Gamow | |
| 5,503,146 A | | 4/1996 | Froehlich et al. | |
| 5,551,419 A | | 9/1996 | Froehlich et al. | |
| 5,560,354 A | | 10/1996 | Berthon-Jones et al. | |
| 5,582,574 A | | 12/1996 | Cramer | |
| 5,645,053 A | | 7/1997 | Remmers et al. | |
| 5,645,054 A | | 7/1997 | Cotner et al. | |
| 5,678,543 A | | 10/1997 | Bower | |
| 5,682,878 A | | 11/1997 | Ogden | |
| 5,682,881 A | | 11/1997 | Winthrop et al. | |
| 5,687,715 A | | 11/1997 | Landis et al. | |

(Continued)

FOREIGN PATENT DOCUMENTS

CA 2227444 2/1997

(Continued)

OTHER PUBLICATIONS

U.S. Appl. No. 60/443,227, filed Jan. 2003, Thomas et al.*

(Continued)

Primary Examiner—Kevin T Truong
(74) Attorney, Agent, or Firm—Coats & Bennett, P.L.L.C.

(57) ABSTRACT

A CPAP enclosure used in the treatment of Obstructive Sleep Apnea (OSA) comprises a base connected to a bed, a canopy connected to the base, and a sealing member that connects the canopy to the base. The sealing member forms a substantially airtight seal such that the canopy and the base form a substantially airtight enclosure around at least a portion of the bed. A Continuous Positive Airway Pressure (CPAP) compressor connects to the enclosure via flexible tubing, and generates a continuous positive airway pressure within the enclosure to treat a patient having OSA.

8 Claims, 5 Drawing Sheets

U.S. PATENT DOCUMENTS

| | | | | |
|---|---|---|---|---|
| 5,799,652 | A | | 9/1998 | Kotliar |
| 5,832,919 | A | * | 11/1998 | Kano et al. ............ 128/205.26 |
| 5,850,833 | A | | 12/1998 | Kotliar |
| 5,865,722 | A | | 2/1999 | Heng |
| 5,887,439 | A | | 3/1999 | Kotliar |
| 5,924,419 | A | | 7/1999 | Kotliar |
| 5,964,222 | A | * | 10/1999 | Kotliar ................ 128/205.26 |
| 6,062,215 | A | | 5/2000 | Leininger et al. |
| RE36,958 | E | | 11/2000 | Gamow |
| 6,321,746 | B1 | | 11/2001 | Schneider et al. |
| 6,380,859 | B1 | | 4/2002 | Brownlee |
| 6,805,120 | B1 | * | 10/2004 | Jeffrey et al. .......... 128/204.23 |
| 6,854,459 | B1 | * | 2/2005 | Cox ..................... 128/201.23 |
| 2004/0144383 | A1 | * | 7/2004 | Thomas et al. ......... 128/204.18 |

FOREIGN PATENT DOCUMENTS

| EP | 959862 | 11/2001 |
|---|---|---|

OTHER PUBLICATIONS

"Obstructive Sleep Apnea Syndrome." Chokroverty S. in *Sleep Disorders Medicine: Basic Science, Technical Considerations, and Clinical Aspects.* Butterworth and Heinemann, Boston, 1999.

Sullivan, C. and Grunstein, R. "Continuous Positive Airway Pressure for Sleep Related Breating Disorders." *Sleep Medicine,* 3rd ed. Kryger, J., Roth, T., and Dement, W. WB Saunders, Philadelphia, 2000.

Atwood, C. "Positive Pressure Therapy: Theory and Application." *Respiratory Care.* April, vol. 43, No. 4, pp. 307-315.

Grady, D. "Continuous Positive Airway Pressure." *Laboratory Exercises in Respiratory Care.* JB Lippincott, Philadelphia, pp. 511-515, 1987.

National Institute of Health, National Heart, Lung, and Blood Institute. "Facts About Sleep Apnea." NIH Publication No. 95-3798, Sep. 1995. US Department of Health and Human Services.

American Thoracic Society. "Indications and Standards for Use of Nasal Continuous Positive Airway Pressure (CPAP) in Sleep Apnea Syndromes." *American Journal of Respiratory Critical Care Medicine.* vol. 150, pp. 1738-1745, 1994.

American Thoracic Society/American Sleep Disorders Association. "Statement on Health Outcomes Research in Sleep Apnea." *Am. J. Respiratory Critical Care Medicine.* vol. 157, pp. 335-341, 1998.

Loube, D. et al. "Consensus Statement: Indications for Positive Airway Pressure Treatment of Adult Obstructive Sleep Apnea Patients." *Chest,* vol. 115, No. 3, Mar. 1999, pp. 863-866.

Wathen, J. "What's New With CPAP Technology?" *Sleep Review.* Jul./Aug. 2002, Curant Communications, vol. 3, No. 4, pp. 26-32.

American Academy of Sleep Medicine. "Sleep Apnea: Diagnosis and Treatment." AASM, Rochester, MN, 2000.

Harbison, J. et al. "Cardiac Rhythm Disturbances in the Obstructive Sleep Apnea Syndrome: Effects of Nasal Continuous Positive Airway Pressure Therapy." *Chest,* vol. 118, No. 3, Sep. 2000, pp. 591-595.

Galgon, John P. M.D., "Can Snoring Really Be Fatal?" www.doctorsforum.com/oct96/articles/apnea.html, 5 pages.

"New High Altitude Bed Enhances Athletic Performance." www.metzger.com/simula/release1.html, Phoenix, AZ, Mar. 17, 1994, 2 pages.

"Altitude Acclimatization in Non-Exercising Rats." http://spot.colorado.edu/~gamow/research/rats.html. Printed on Jul. 19, 1997, 2 pages.

"The Gamow Bag." http://spot.colorado.edu/~gamow/research/bag.html; Printed Jul. 19, 1997, 1 page.

Hypoxico Home Products, http://www.hypoxico.com/home_sleep.htm, 3 pages.

Hypoxico More Information, http://www.hypoxico.com/info.htm, 2 pages.

* cited by examiner

US 7,520,277 B1

CPAP ENCLOSURE FOR THE TREATMENT OF SLEEP APNEA

BACKGROUND OF THE INVENTION

The present invention relates generally to medical devices, and in particular, to medical devices used in the treatment of Obstructive Sleep Apnea (OSA).

OSA is a type of sleep disorder that produces altered breathing functions during sleep. Patients who suffer from OSA experience a partial or complete airway obstruction during sleep, resulting in decreased airflow and sleep fragmentation. This adversely affects respiratory, cardiac, and neurological functions, and often causes patients to experience excessive daytime drowsiness. When left untreated, OSA may result in long-term health problems such as hypertension, stroke, cardiac arrhythmias, and myocardial infarction.

One way to treat patients suffering from OSA is to apply a Continuous Positive Airway Pressure (CPAP) to the patient while they sleep. The positive pressure functions as a pneumatic stent that prevents the collapse of the upper airway. Current devices typically apply CPAP by way of a mask secured to the patient's head. While effective, such treatment is not without problems. For example, masks may result in irritation, nasal congestion, and nosebleeds. Other side effects may include a loss of positive pressure from displaced or poorly fitted masks. These side effects, and others like them, may be factors that contribute to the relatively low percentage of patient compliance with current CPAP treatments. Therefore, there is a need for an improved system and method of administering CPAP to patients suffering from OSA.

SUMMARY OF THE INVENTION

A CPAP enclosure used in the treatment of Obstructive Sleep Apnea (OSA) comprises an airtight enclosure that surrounds at least a portion of a bed. The enclosure includes a base, a canopy connected to the base, and a sealing member that connects the canopy to the base. The sealing member forms a substantially airtight seal between the canopy and the base. A Continuous Positive Airway Pressure (CPAP) compressor connects to the enclosure via flexible tubing, and generates a continuous positive airway pressure within the enclosure to treat a patient having OSA.

In one embodiment, the patient enters the enclosure through an access door, lies down on the bed, and seals the access door closed. The CPAP compressor generates the continuous positive airway pressure within the enclosure, which is regulated by a pressure valve and monitored using a manometer. The continuous positive pressure prevents collapse of the patients upper airway, and facilitates uninterrupted sleep for the patient without the need for a fitted mask.

DETAILED DESCRIPTION OF THE INVENTION

Figure 1:
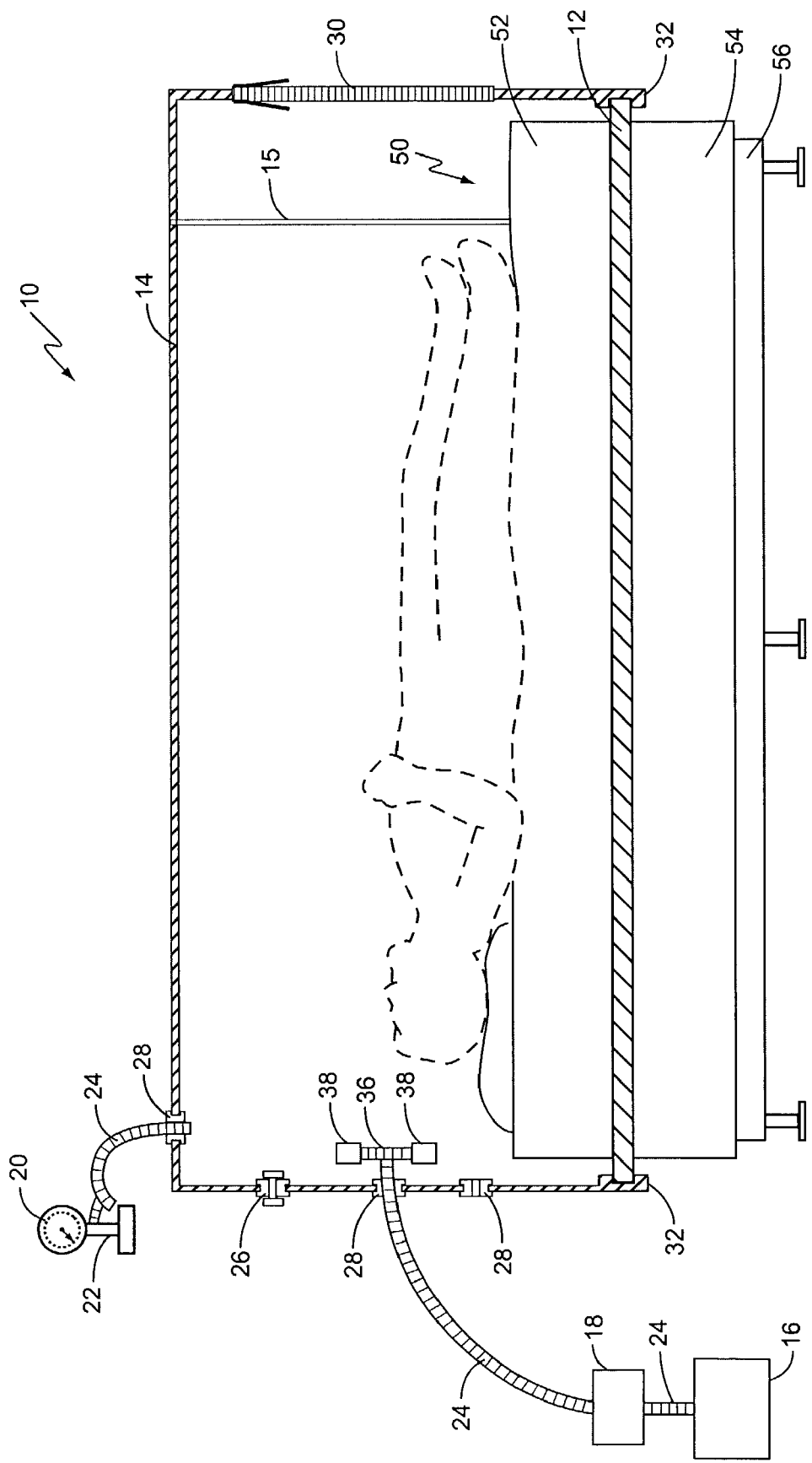
FIG. 1 illustrates a patient afflicted with OSA using one embodiment of the present invention.

Referring now to FIG. 1, the CPAP enclosure of the present invention is shown therein and indicated generally by the number 10. CPAP enclosure 10 comprises a base 12, a canopy 14 releasably coupled to the base 12, and a CPAP compressor 16. A first sealing member 32 couples the base 12 to the canopy 14, and forms a substantially airtight seal between canopy 14 and base 12. When base 12 is coupled to canopy 14, a substantially air-tight sleep enclosure 10 is formed that extends around at least a portion of bed 50.

Flexible non-kink tubing 24 connects compressor 16, an optional humidifier 18, and a manometer 20 to enclosure 10 through one or more airtight ports 28 disposed in the sidewalls of canopy 14. The humidifier 18 conditions the air output by compressor 16 by controlling its relative humidity. The inspired air may further be temperature controlled, if desired, by one or more heated wires (not shown) within flexible tubing 24. A T-adaptor 36 having one or more heat exchange filters 38 is disposed within enclosure 10.

Canopy 14 may be constructed from a lightweight, flexible, non-allergenic, puncture resistant material, such as acrylic, polyethylene, or 18-guage PVC with vinyl, although it should be understood that canopy 14 is not limited only to these materials. Further, the material used to construct canopy 14 may attenuate sound and/or light to facilitate sleeping, and may be constructed as a single piece, or alternatively, may comprise a plurality of panels fused together. The material used for the canopy 14 may be sufficiently rigid so as to be substantially self-supporting absent continuous pressure inside the canopy 14. Alternatively, canopy 14 may be made of a flexible sheet material that is supported by support rings 15 that prevent the collapse of canopy 14 in the event of sudden depressurization.

One or more airtight ports 28 formed in the sidewalls of canopy 14 maintain positive air pressure within enclosure 10, while providing access for flexible tubing 24, various wires and cables that lead to equipment used in diagnostic sleep studies, and cables used by specialty beds. Further, one or more emergency one-way air intake valves 26 may also be disposed in the sidewall of canopy 14. The one-way air intake valves 26 are designed to open should enclosure 10 experience a sudden depressurization and/or failure of compressor 16. The air intake valve 26 should be operable to provide a patient with an adequate supply of fresh air, and prevent inadvertent suffocation of the patient.

FIG. 1 illustrates one embodiment wherein base 12 is disposed between the mattress 52 and boxspring 54 of a bed, and projects outward from the periphery of mattress 52. Base 12 may be constructed of an airtight acrylic or plastic material, and may be formed as a single piece or a plurality of panels that are fitted together. In this embodiment, the first sealing member 32, constructed of rubber or other elastic material, is connected to the bottom edge of canopy 14. When mated with base 12, the first sealing member 32 forms a substantially airtight seal between base 12 and canopy 14. This airtight seal permits canopy 14 and base 12 to form the substantially airtight sleeping enclosure 10 around at least a portion of bed 50.

A patient being treated for OSA may access enclosure 10 through an access door disposed in a sidewall of canopy 14. In this embodiment, the access door comprises a double-sided zipper 30 operable from both inside and outside of enclosure 10, and seals enclosure 10 so that it remains substantially airtight. Other embodiments may include a "ZIP-LOC" type zipper (not shown), or the two-way type of seal used in underwater wetsuits (not shown). Whatever type of zipper or seal is used, it should permit a patient to operate it from both inside and outside enclosure 10.

The CPAP compressor 16 is connected to an external power source (not shown), and generates a continuous positive airway pressure used to treat patients afflicted with OSA. CPAP compressor 16 operates by compressing a gas (e.g., air), and delivering it to the interior of enclosure 10 via flexible tubing 24. The compressor 16 is capable of generating the continuous positive airway pressure in a range much lower than that of known hyperbaric chambers. In one embodiment, compressor 16 generates a continuous positive airway pressure within enclosure 10 in the low range of about 0-40 cm. $H_2O$, and preferably in the range of about 0-30 cm $H_2O$. Although these ranges are exemplary, those skilled in the art will realize that the pressures created by compressor 16 are radically lower than the pressures of 2000-3000 cm. $H_2O$ typically created by known hyperbaric chambers. These higher pressures found in hyperbaric chambers require the chambers to be built of heavy, often multi-layered and expensive materials that can withstand intense pressure. Further, the high pressures generated by known hyperbaric chambers generally require prolonged periods for decompression for entry/exit from the enclosure, and generate very high noise levels. Thus, they are unsuitable for sleep and the treatment of sleep related disorders.

Compressor 16 may be turbine driven to reduce noise generation, and further, may be capable of generating airflow rates that are about 2-4 times greater than the patient's exhaled minute volume. In one embodiment, this produces a total airflow through the enclosure 10 of about 10-40 liters/minute, and preferably about 20-30 liters/minute. This range of airflow rate through enclosure 10 effectively flushes the patient's exhaled carbon dioxide to the outside atmosphere, and helps reduce re-breathing of exhaled gasses. Further, the flow rate from compressor 16 is adjustable to completely prevent carbon dioxide re-breathing, as well as to facilitate certain types of patient monitoring in a diagnostic sleep lab, for example, capnography monitoring.

Figure 2:
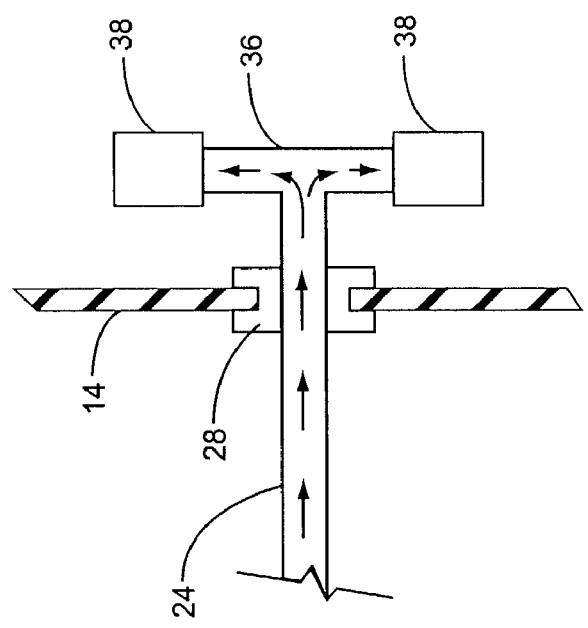
FIG. 2 illustrates an exemplary T-adaptor used in one embodiment of the present invention.

The compressor 16 connects to a T-adapter 36 that lies within enclosure 10 via flexible tubing 24 that passes through the airtight port 28. As seen in FIG. 2, the T-adapter 36 may include one or more heat-moisture exchange filters 38 to maintain sound and humidity at acceptable levels within enclosure 10. One type of T-adapter 36 used in the present invention is a standard Briggs T-adapter, although those skilled in the art will readily appreciate that other types of adapters 36 may also be used.

Figure 3:
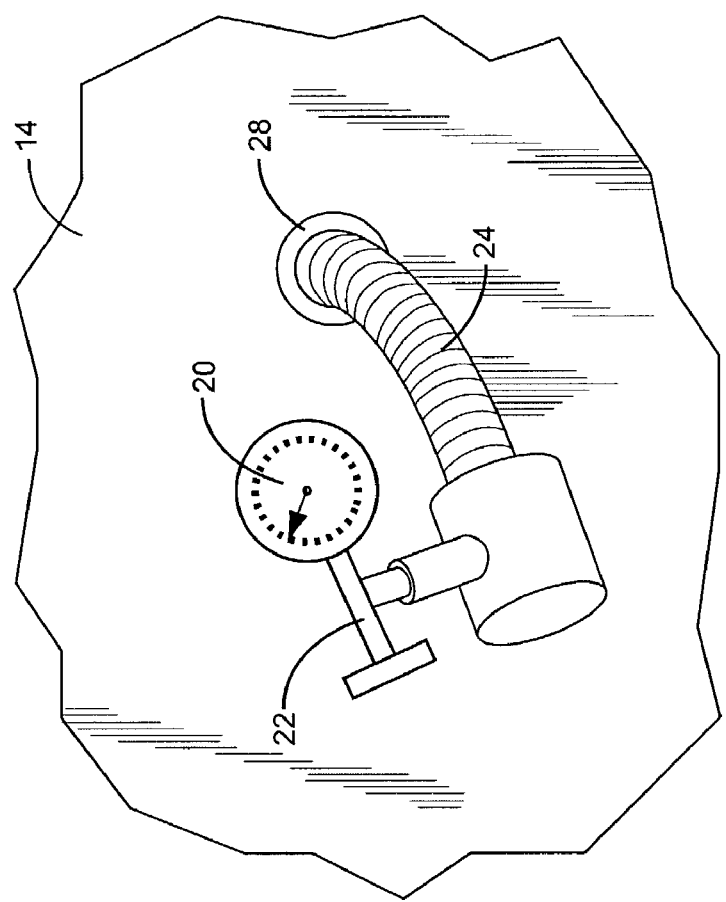
FIG. 3 illustrates an exemplary manometer and pressure valve used in one embodiment of the present invention.

A manometer 20, shown in FIG. 3, is used to monitor the continuous positive airway pressure inside enclosure 10. A variable pressure release valve 22 regulates the amount of positive pressure by restricting the opening in which the air inside enclosure 10 can exit. In one embodiment, manometer 20 and valve 22 are shown as a single entity, and are connected to a sidewall of canopy 14 via flexible tubing 24. However, those skilled in the art will readily understand that manometer 20 and valve 22 may exist as separate parts, and further, may connect to enclosure 10 through airtight ports 28 in either the canopy 14 or base 12.

Figure 4:
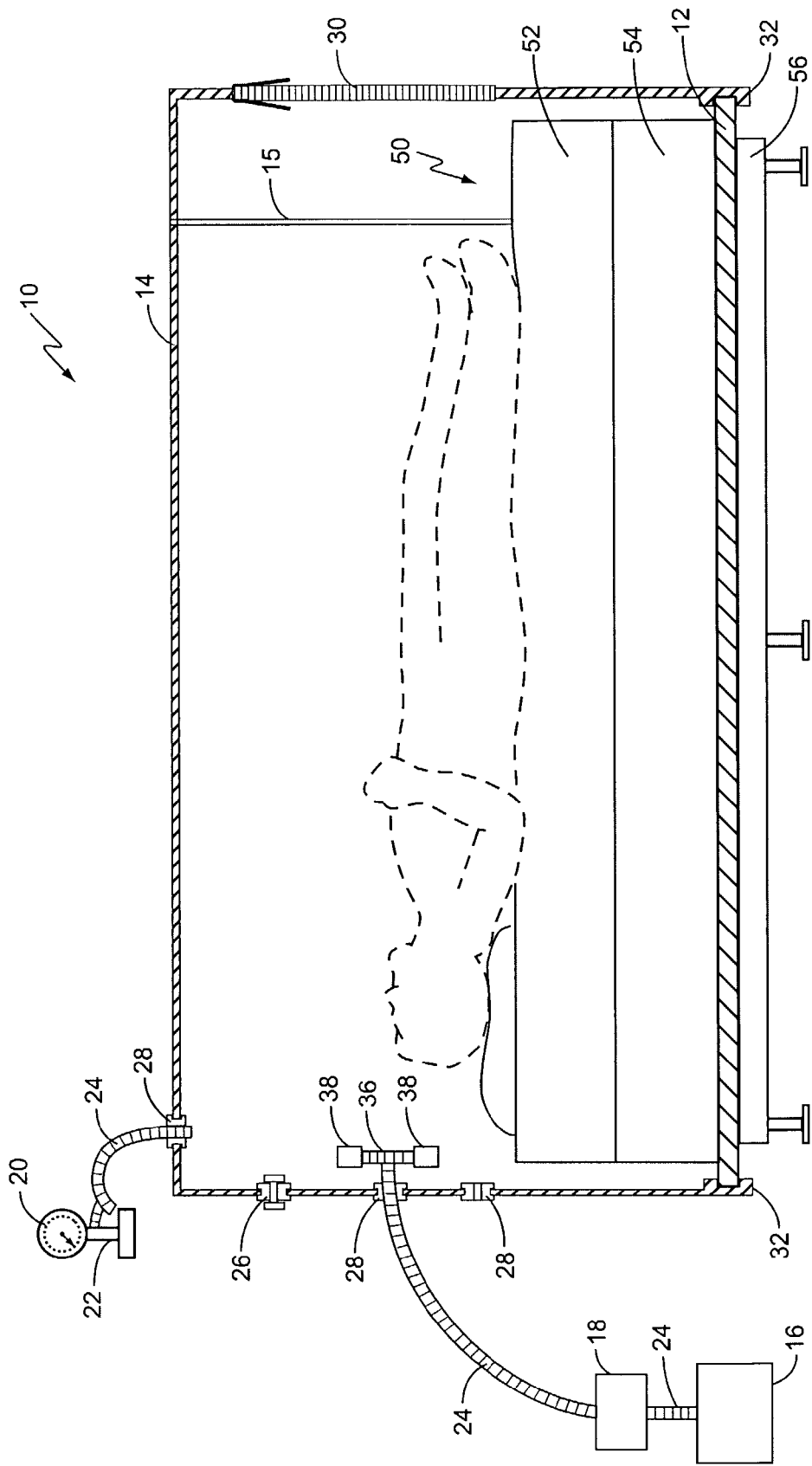
FIG. 4 illustrates the patient using an alternate embodiment of the present invention.

FIG. 4 illustrates an alternate embodiment of the present invention wherein base 12 is disposed between the boxspring 54 and the frame of the bed 56. The first sealing member 32 is disposed on the bottom edges of canopy 14, and forms the substantially airtight seal with base 12. More specifically, the first sealing member 32 engages the outer edge of base 12 to form an airtight seal. Although the position of base 12 may vary, those skilled in the art will understand that this does not adversely affect the operability of enclosure 10. That is, the first sealing member 32 disposed on the bottom edges of canopy 14 forms the substantially airtight seal between the canopy 14 and base 12. As such, the canopy 14 and base 12 form the substantially airtight sleeping enclosure 10 around at least a portion of the patient's bed 50.

Figure 5:
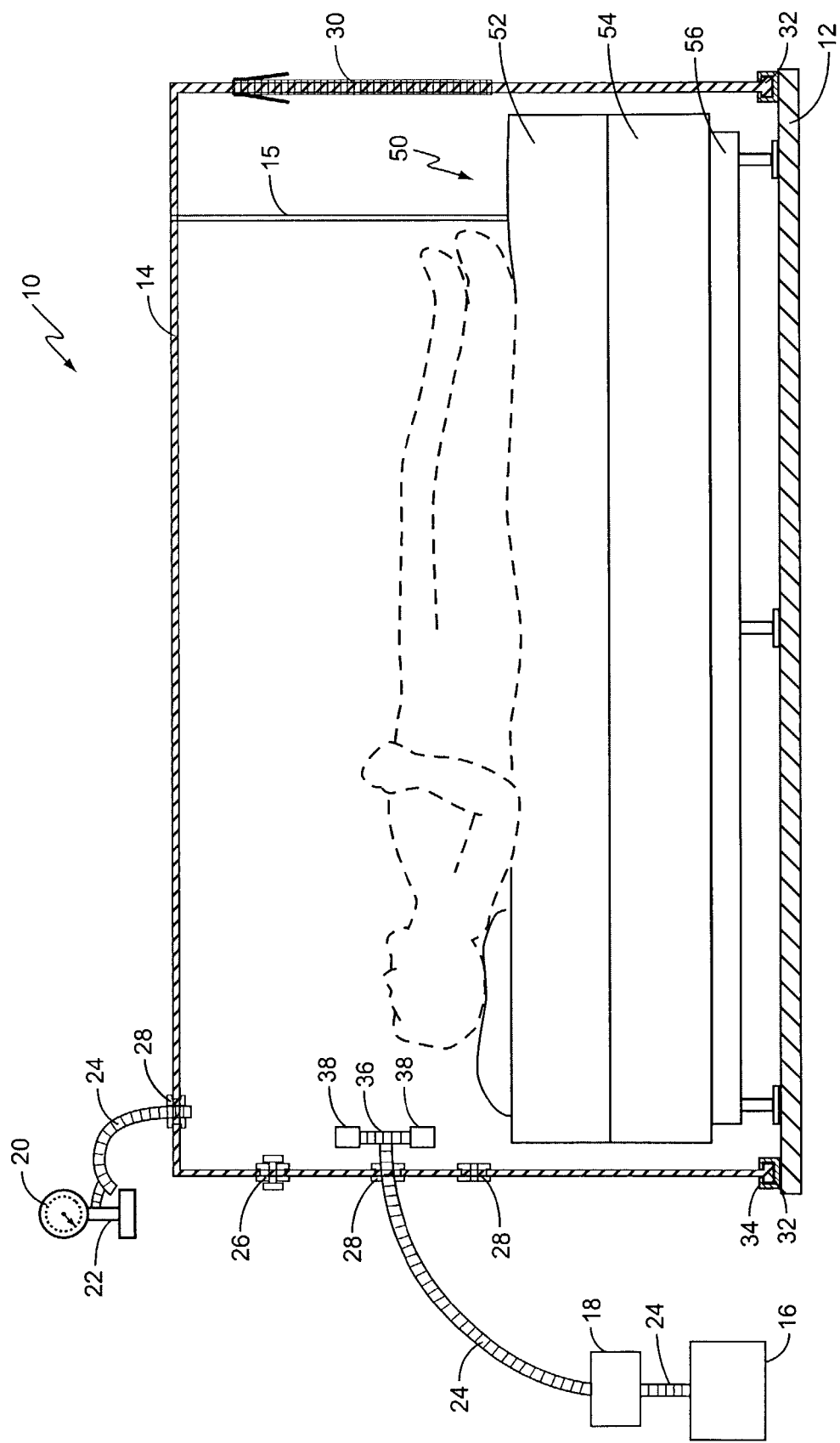
FIG. 5 illustrates the patient using yet another embodiment of the present invention.

In another alternate embodiment shown in FIG. 5, base 12 is positioned under the frame 56 of bed 50. In this embodiment, the first sealing member 32 mates with a second sealing member 34 disposed on base 12, and forms the substantially airtight seal around base 12. The position of base 12 in this embodiment creates a substantially airtight enclosure 10 around the patient's entire bed.

Those skilled in the art will appreciate that base 12 need not be secured or attached to bed 50. However, depending on the type of bed 50 that enclosure 10 encloses, it may be more efficient to secure base 12 to bed 50. For example, it may be sufficient to simply dispose base 12 between the mattress 52 and boxspring 54, or between the boxspring 54 and frame 56, in a typical bed 50. In these embodiments, the weight of the patient together with the weight of the mattress 52 and/or boxspring 54 may be sufficient to stabilize the base 12 and prevent it from shifting or moving. Thus, inadvertent radical movement by the patient during sleep will not compromise the airtight seal around base 12.

However, other embodiments may be better adapted for situations where enclosure 10 is required to enclose specialty beds (e.g., beds that are operable to elevate all or a portion of the mattress 52, such as those found in hospitals and diagnostic labs). In these cases, mechanical fasteners (not shown) may be used to secure base 12 to frame 54, and therefore stabilize base 12 regardless of the position of the mattress 52. Whatever the embodiment, enclosure 10 should form a substantially airtight enclosure around at least a portion of bed 50, and provide the patient with a sleeping enclosure that is comfortable and has adequate area in which to move freely.

Figure 6C:
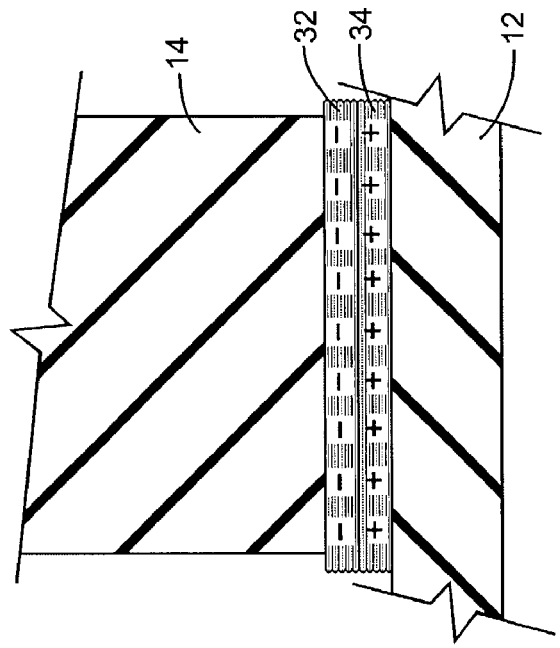
FIGS. 6A-6C illustrate exemplary sealing members used in various embodiments of the present invention.
Figure 6B:
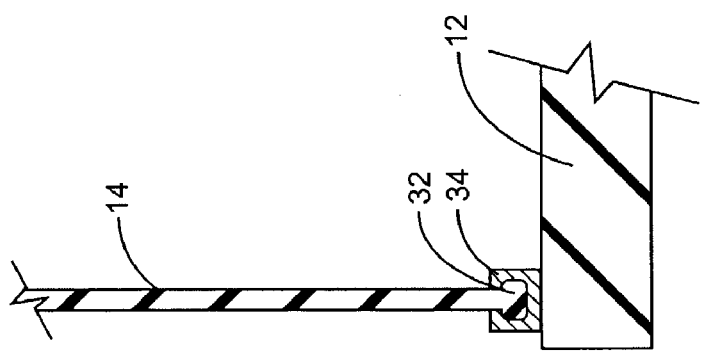
Figure 6A:
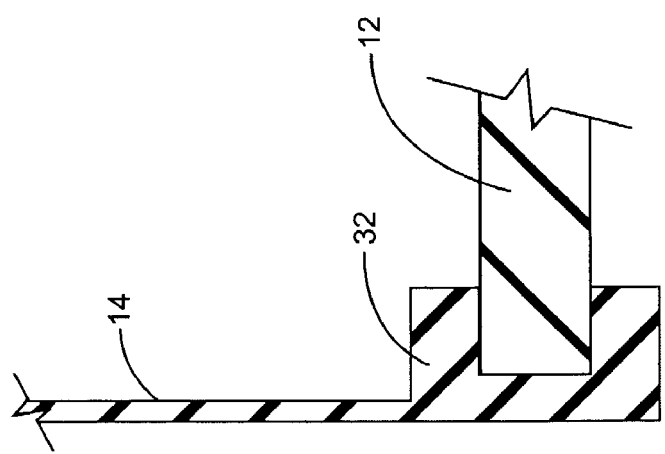

FIGS. 6A-6C illustrate various configurations for the first and second sealing members 32, 34. FIG. 6A illustrates one embodiment of the first sealing member 32 connected to the bottom edges of canopy 14, thereby terminating the sidewalls of canopy 14. The first sealing member 32 is elastic and substantially U-shaped, and receives the outer edges of base 12. To form the airtight seal between canopy 14 and base 12, a patient merely pushes the first sealing member 32 onto the edges of base 12.

FIG. 6B illustrates the first and second sealing members 32, 34 that may be used in the embodiment of FIG. 5, for example. Here, first sealing member 32 is shaped differently, but still terminates the bottom edges of canopy 14. The second sealing member 34 is disposed on the base 12, and receives the first sealing member 32 in a manner similar to that of a "ZIP-LOC" seal. That is, a user aligns the first and second sealing members 32, 34, and pushes the first sealing member 32 into the receiving portion of second sealing member 34. In some embodiments, the first sealing member 32 may be slightly rigid to facilitate insertion of the first and second sealing members 32, 34.

Another embodiment of the first and second sealing members 32, 34 is shown in FIG. 6C. In this embodiment, the first and second sealing members 32, 34 are disposed on the bottom edge of canopy 14 and base 12, respectively, but assume the form of magnetic rubber strips having opposing polarities. The opposite polarities of the first and second sealing members 32, 34 attract each other, thereby forming the substantially airtight seal around between canopy 14 and base 12. Thus, base 12 and canopy 14 forms the substantially airtight enclosure 10.

To treat a person afflicted with a sleep disorder, such as OSA, the user first forms the enclosure 10 by coupling the canopy 14 to base 12, and forming a substantially airtight enclosure that surrounds at least a portion of the patient's bed 50. The first and/or second sealing members form the substantially airtight seal between the canopy 14 and base 12, as described above. The patient, or another user, operates compressor 16 such that it generates a positive air pressure within enclosure 10. Once a desired pressure is reached, the patient enters through the access door, and closes the double-sided zipper 30. The patient is now free to lie down and sleep. As the patient sleeps, the CPAP compressor 16 generates and maintains a continuous positive airway pressure within the interior of enclosure 10.

Those skilled in the art will readily appreciate many variations may be made to the present without departing from its scope. For one, the CPAP compressor may deliver other types of gas to the interior of enclosure 10 in addition to (or in place of) air. Further, the embodiments illustrated in the drawings show the canopy 14 permitting access into the enclosure via the airtight ports 28. However, the one-way air intake valve 26 and airtight ports 28 may actually be disposed in either the base 12 or canopy 14 or both. Additionally, mechanical fasteners, for example, bolts and/or screws, may be used to secure to the bed frame 56.

The present invention may of course, be carried out in other specific ways than those herein set forth without departing from the essential characteristics of the invention. The present embodiments are, therefore, to be considered in all respects as illustrative and not restrictive and all changes coming within the meaning and equivalency range of the appended claims are intended to be embraced therein.

What is claimed is:

1. A CPAP enclosure for treating a patient having Obstructive Sleep Apnea (OSA) comprising:
   a substantially air-tight enclosure configured to enclose the head of a patient suffering from OSA and surround at least a portion of a bed;
   a Continuous Positive Airway Pressure (CPAP) compressor coupled to said enclosure; and
   said CPAP compressor generating a continuous positive airway pressure within said enclosure to treat the patient suffering from OSA.

2. The enclosure of claim 1 further comprising a pressure valve attached to said enclosure.

3. The enclosure of claim 2 further comprising a manometer coupled to said pressure valve.

4. The enclosure of claim 1 further comprising a one-way air intake valve disposed in a sidewall of said enclosure that opens upon failure of said CPAP compressor.

5. A method of treating a patient having Obstructive Sleep Apnea (OSA) comprising:
   forming a substantially airtight enclosure around at least a portion of the patient's bed;
   generating a continuous positive airway pressure within said enclosure to treat the patient having OSA.

6. The method of claim 5 wherein generating a continuous positive airway pressure comprises inflating said enclosure with a Continuous Positive Airway Pressure (CPAP) compressor connected to said enclosure.

7. A CPAP enclosure for treating a patient having Obstructive Sleep Apnea (OSA) comprising:
   a substantially air-tight enclosure configured to enclose the head of a patient suffering from OSA and at least partially surround a sleeping surface;
   a Continuous Positive Airway Pressure (CPAP) compressor coupled to said enclosure to generate a continuous positive airway pressure within said enclosure to treat the patient suffering from OSA.

8. The enclosure of claim 7 wherein the sleeping surface comprises a mattress on which the patient sleeps.

\* \* \* \* \*